United States Patent
Nagel et al.

(10) Patent No.: US 12,241,046 B2
(45) Date of Patent: *Mar. 4, 2025

(54) USE OF UREA OR A UREA/CHELATOR COMBINATION TO CHEMICALLY STABILIZE PEROXYCARBOXYLIC ACID AND PEROXIDE FORMULATIONS

(71) Applicant: ECOLAB USA INC., Saint Paul, MN (US)

(72) Inventors: Chris Nagel, Saint Paul, MN (US); Junzhong Li, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/408,068

(22) Filed: Jan. 9, 2024

(65) Prior Publication Data
US 2024/0141261 A1  May 2, 2024

Related U.S. Application Data

(63) Continuation of application No. 17/248,919, filed on Feb. 12, 2021, now Pat. No. 11,905,498.

(60) Provisional application No. 62/975,340, filed on Feb. 12, 2020.

(51) Int. Cl.
| | |
|---|---|
| C11D 3/20 | (2006.01) |
| A01N 25/22 | (2006.01) |
| A01N 59/00 | (2006.01) |
| C11D 3/04 | (2006.01) |
| C11D 3/32 | (2006.01) |
| C11D 3/34 | (2006.01) |
| C11D 3/36 | (2006.01) |
| C11D 3/39 | (2006.01) |

(52) U.S. Cl.
CPC .............. *C11D 3/394* (2013.01); *A01N 25/22* (2013.01); *A01N 59/00* (2013.01); *C11D 3/042* (2013.01); *C11D 3/2075* (2013.01); *C11D 3/2079* (2013.01); *C11D 3/32* (2013.01); *C11D 3/3409* (2013.01); *C11D 3/361* (2013.01); *C11D 3/3902* (2013.01); *C11D 3/3942* (2013.01); *C11D 3/3945* (2013.01)

(58) Field of Classification Search
CPC ....... C11D 3/32; C11D 3/3942; C11D 3/3945; C11D 3/2079; C11D 3/2075; C11D 3/3902

USPC .......... 510/372, 477, 488, 499, 501
See application file for complete search history.

(56) References Cited

U.S. PATENT DOCUMENTS

| | | | |
|---|---|---|---|
| 3,442,937 A | 5/1969 | Sennewald et al. | |
| 3,766,078 A | 10/1973 | Kowalski | |
| 4,129,517 A | 12/1978 | Eggensperger et al. | |
| 4,155,738 A | 5/1979 | Boghosian | |
| 5,922,307 A | 7/1999 | Montgomery | |
| 10,344,199 B2 | 7/2019 | Pisanova et al. | |
| 11,905,498 B2 * | 2/2024 | Nagel | C11D 3/042 |
| 2003/0211169 A1 | 11/2003 | Tabasso | |
| 2006/0003028 A1 | 1/2006 | Myers et al. | |
| 2017/0210969 A1 | 7/2017 | Pisanova et al. | |
| 2019/0045789 A1 | 2/2019 | Daigle | |
| 2019/0208774 A1 | 7/2019 | Lei et al. | |

FOREIGN PATENT DOCUMENTS

| | | |
|---|---|---|
| CN | 1081568 A | 2/1994 |
| CN | 102613179 A | 8/2012 |
| CN | 105724381 A | 7/2016 |
| DE | 2038485 A1 | 2/1972 |
| EP | 2095714 A2 | 9/2009 |
| EP | 2579722 B1 | 11/2016 |
| EP | 3574758 A1 | 12/2019 |
| WO | 0027439 A1 | 5/2000 |
| WO | 03011347 A1 | 2/2003 |
| WO | 2004026770 A1 | 4/2004 |
| WO | 2009075663 A1 | 6/2009 |

OTHER PUBLICATIONS

International Searching Authority in connection with PCT/US2021/017759 filed Feb. 12, 2021, "The International Search Report and the Written Opinion of the International Searching Authority, or the Declaration", 15 pages, mailed Apr. 30, 2021.

* cited by examiner

*Primary Examiner* — Gregory R Delcotto
(74) *Attorney, Agent, or Firm* — McKee, Voorhees & Sease, PLC

(57) ABSTRACT

Stabilized peroxide-containing compositions stabilized with urea and urea/chelator stabilizer blends are provided. The compositions are particularly suitable for, but not limited to, cleaning applications on surfaces within food and beverage industries which may require the use of materials that are acceptable for incidental food/food products/feed contact. Further, the stabilized compositions are particularly suitable for applications requiring materials that are generally regarded as safe (GRAS) or for applications where non-GRAS materials must be minimized. Methods of stabilizing peroxide-containing compositions and methods of using the compositions are also provided.

19 Claims, No Drawings

USE OF UREA OR A UREA/CHELATOR COMBINATION TO CHEMICALLY STABILIZE PEROXYCARBOXYLIC ACID AND PEROXIDE FORMULATIONS

CROSS REFERENCE TO RELATED APPLICATION

This is a Continuation application of U.S. Ser. No. 17/248,919, filed Feb. 12, 2021, which claims priority under 35 U.S.C. § 119 to U.S. Provisional Application Ser. No. 62/975,340, filed Feb. 12, 2020. Provisional Application No. 62/975,340 is herein incorporated by reference in its entirety.

FIELD OF THE INVENTION

The present disclosure relates to peroxide and peroxycarboxylic acid compositions that are liable to exothermic decomposition which are stabilized with urea and urea/chelator stabilizer blends. The compositions are particularly suitable for, but not limited to, cleaning applications on surfaces within food and beverage industries which may require the use of materials that are acceptable for incidental food/food products/feed contact. Still further, the stabilized compositions are particularly suitable for applications requiring materials that are generally regarded as safe (GRAS) or for applications where non-GRAS materials must be minimized.

BACKGROUND OF THE INVENTION

Peroxides and peroxycarboxylic acids (i.e., peracids, such as peracetic acid) are components which are increasingly utilized as antimicrobial and bleaching agents in a variety of industries. Peroxycarboxylic acid compositions are further favorable owing to their broad biocidal efficacy and excellent environmental profiles. However, both peroxides and peroxycarboxylic acids fall into the chemical category of "organic peroxides" which in turn are classified as self-reactive, self-heating substances due to their oxidizing activity. For example, pure peroxycarboxylic acids, such as a peracetic acid, are unstable and may lead to explosive activity if not stabilized. Thus, commercially available peroxycarboxylic acids are usually sold in an equilibrium solution, wherein the equilibrium solution also contains the corresponding carboxylic acid, hydrogen peroxide, and water.

When oxidizing compounds such as peroxides and peroxycarboxylic acids are incorporated into use compositions (i.e., cleaning compositions, sanitizing compositions, antimicrobial compositions, etc.) the compositions are inherently unstable. To enhance the chemical stability, various stabilizers are included to stabilize the compositions. Such stabilizing agents are commonly molecules that complex transition metals or quench radical species as they are generated. However, identifying suitable stabilizing agents can be a unique challenge, as very few materials are effective and/or stable in compositions containing strong acids and strong oxidizers while also encompassing toxicity profiles acceptable for its intended applications of use.

Various stabilizers have been used in compositions containing oxidizing compounds to stabilize the compositions. For example, pyridine carboxylic acid-based stabilizers, such as picolinic acid and salts, pyridine-2,6-dicarboxylic acid and salts, and phosphonate-based stabilizers, such as phosphoric acid and salts, pyrophosphoric acid and salts, and most commonly 1-hydroxyethylidene-1,1-diphosphonic acid (HEDP) and salts, have been used as conventional stabilizers. When used individually at sufficient concentrations, these stabilizers improve the stability of the peroxycarboxylic acid compositions. For the peroxycarboxylic acid compositions, the stability profile achieved with these conventional stabilizers allow for their commercial use.

Among the various stabilizers, peroxycarboxylic acid compositions may be stabilized by chelating residual transition metal ions in the formulation to prevent catalytic decomposition of hydrogen peroxide into radical species. For example, HEDP, a widely employed chelator, has been shown to degrade completely within months, leaving the metal ions to return to solution and become active catalysts. Furthermore, dipicolinic acid (DPA) is often used as a synergistic stabilizer for stabilizing compositions containing oxidizing compounds.

Without being limited to a particular theory or mechanism, DPA functions as a stabilizer through radical scavenging of outstanding radicals despite the use of an additional stabilizer, such as HEDP. DPA provides synergistic activity by scavenging radicals to protect the additional stabilizer, and other materials, while the additional stabilizer prevents radicals from forming. Therefore, DPA is often utilized as a stabilizing agent due to its efficacious synergistic stabilizing activity with additional stabilizing agents. However, there remains a disadvantage to the use of picolinic acid stabilizers, such as DPA, due to its cost. Therefore, there remains a need for cost effective stabilizing agents that are efficacious in stabilizing strong oxidizing compounds, such as peroxides and peroxycarboxylic acids.

In addition, the use of chemicals including stabilizers used in compositions comprising oxidizing compounds for food contact—both direct and indirect food/feed contact—are very strict with requirements for compositions that are safe for food contact. Stabilizing agents including pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts, and most commonly 1-hydroxyethylidene-1,1-diphosphonic acid (HEDP) and salts, have not been classified as a food ingredient, therefore rendering limitations on the amount of these stabilizing agents that can be used on food or plant products for human or animal consumption. Further, the U.S. Food and Drug Administration (FDA) has narrow limitations on the quantity of HEDP permitted in food and plant products for animal or human consumption, making it difficult to utilize sufficient concentrations of HEDP to be effective as a single stabilizing agent in compositions that must be safe for food contact. See, for example, 21 C.F.R. § 173.370. Therefore, there is an ongoing need for providing peroxide and peroxycarboxylic acid compositions having none, or reduced concentrations of phosphonic acid-based stabilizers, while maintaining stability.

Accordingly, it is an objective of the disclosure herein to provide alternative stabilizing agents to dipicolinic acid in compositions comprising strong acids and strong oxidizing agents to maintain cost effective ingredients.

A further object of the disclosure is to provide stabilized peroxide and peroxycarboxylic acid compositions which are safe and efficacious for applications having direct or incidental food/feed contact.

A still further object of the disclosure is to develop stabilized peroxycarboxylic acid compositions that are free of phosphonic acids, such as HEDP, or that reduce the amount of HEDP included in the composition while maintaining a composition that stabilizes compositions comprising oxidizing compounds.

Other objects, advantages and features of the present disclosure will become apparent from the following specification.

BRIEF SUMMARY OF THE INVENTION

The present disclosure relates to stable peroxide and peroxycarboxylic acid compositions and uses thereof. An advantage of the disclosure includes stabilizing highly oxidative compositions comprising peroxides and/or peroxycarboxylic acid compositions, including mixed peroxycarboxylic acids, utilizing urea and urea/chelator blends. It is an advantage of the present disclosure that the urea provides considerable stabilizing effects on oxidizing compounds, while providing considerable cost reductions compared to formulations containing dipicolinic acid (DPA). Further, the urea and urea/chelator stabilizer blends provide effective stabilizing alternatives for food or animal feed applications, as DPA is not typically suitable for such use.

In an embodiment, a stabilized peroxide-containing composition at equilibrium is provided. The stabilized peroxide-containing composition at equilibrium comprises: an oxidizing compound comprising hydrogen peroxide; a stabilizing agent comprising urea; water; and optionally an additional stabilizing agent, wherein the urea reduces the concentration of the additional stabilizing agent to less than 3 wt-%. Beneficially, the stabilized peroxide-containing composition is substantially free of a pyridine carboxylic acid comprising 2,6-pyridinecarboxylic acid.

In a further embodiment, a food safe stabilized, equilibrium peroxide-containing composition comprising: hydrogen peroxide; a $C_1$-$C_{22}$ peroxycarboxylic acid;

a $C_1$-$C_{22}$ carboxylic acid; a stabilizing agent comprising urea; an acid additive comprising an organic acid, an inorganic acid, or a combination thereof; and water, wherein the urea reduces the concentration of the additional stabilizing agent to less than 3 wt-%, is provided.

In a further embodiment, a method of stabilizing a peroxide-containing composition is provided. The method comprises: combining an oxidizing compound comprising hydrogen peroxide, a stabilizing agent comprising urea, and water; wherein at least 80% of the oxidizing compound concentration is retained after storage of up to one year at room temperature. The peroxide-containing composition may further comprise a $C_1$-$C_{22}$ carboxylic acid, a $C_1$-$C_{22}$ peroxycarboxylic acid, and an acid additive comprising an organic acid and/or inorganic acid. Further, an additional stabilizing agent comprising HEDP may be included, wherein the urea stabilizing agent reduces the concentration of HEDP by at least 40% compared to a composition free of urea as the stabilizing agent.

In a still further embodiment, a method of using a stabilized peroxide-containing composition comprising: providing a peroxide-containing composition comprising an oxidizing compound comprising hydrogen peroxide, a stabilizing agent comprising urea, and water; contacting a surface or substrate with a use solution of the peroxide-containing composition; and cleaning and/or sanitizing the surface or substrate.

While multiple embodiments are disclosed, still other embodiments of the present disclosure will become apparent to those skilled in the art from the following detailed description, which shows and describes illustrative embodiments of the disclosure. Accordingly, the detailed description is to be regarded as illustrative in nature and not restrictive.

DETAILED DESCRIPTION OF INVENTION

The present disclosure relates to stabilized compositions comprising oxidizing compounds such as peroxides and/or peroxycarboxylic acids. The compositions have advantages over other stabilization compositions including stabilization efficacy, cost effectiveness, and safety with direct or indirect food contact. The embodiments of this disclosure are not limited to particular compositions, methods of stabilizing and methods of use which can vary and are understood by skilled artisans.

It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 1.5, 2, 2.75, 3, 3.80, 4, 5, and 6. This applies regardless of the breadth of the range.

So that the present disclosure may be more readily understood, certain terms are first defined. Unless defined otherwise, all technical and scientific terms used herein have the same meaning as commonly understood by one of ordinary skill in the art to which embodiments pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2).

As used herein, the term "free," "no," "substantially no" or "substantially free" refers to a composition, mixture, or ingredient that does not contain a particular compound or to which a particular compound or a particular compound-containing compound has not been added. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the phrase "food processing surface" or "food surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, auto dish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw. Food products include many animal feeds.

The term "generally recognized as safe" or "GRAS," as used herein refers to components classified by the Food and Drug Administration as safe for direct human food consumption or as an ingredient based upon current good manufacturing practice conditions of use, as defined for example in 21 C.F.R. Chapter 1, § 170.38 and/or 570.38. Under 21 CFR § 170.30(b), general recognition of safety through scientific procedures requires the same quantity and quality of scientific evidence as is required to obtain approval of the substance as a food additive and ordinarily is based upon published studies, which may be corroborated by unpublished studies and other data and information. U.S. EPA exemptions for active and inert ingredients in contact with food are codified at 40 C.F.R. Chapter 180 and requires that the amounts indicated are safe for human consumption.

The term "hard surface" refers to a solid, substantially non-flexible surface such as a countertop, tile, floor, wall, panel, window, plumbing fixture, kitchen and bathroom furniture, appliance, engine, circuit board, and dish. Hard surfaces may include for example, health care surfaces and food/plant/animal processing surfaces.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

For the purpose of this patent application, successful microbial reduction is achieved when the microbial populations are reduced by at least about 50%, or by significantly more than is achieved by a wash with water. Larger reductions in microbial population provide greater levels of protection. Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, the term "sanitizer" refers to an agent that reduces the number of bacterial contaminants to safe levels as judged by public health requirements. In an embodiment, sanitizers for use in the compositions and methods will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present disclosure are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present disclosure may comprise, consist essentially of, or consist of the components and ingredients of the present disclosure as well as other ingredients described herein. As used herein, "consisting essentially of" means that the methods and compositions may include additional steps, components, or ingredients, but only if the additional steps, components, or ingredients do not materially alter the basic and novel characteristics of the claimed methods and compositions.

Stabilized Peroxide-Containing Compositions

While an understanding of the mechanism is not necessary to practice the present disclosure and while the present disclosure is not limited to any particular mechanisms of action, it is contemplated that, in some embodiments, urea functions similar to dipicolinic acid (DPA) in stabilizing compositions comprising oxidizing agents through its radical scavenging activity. According to an embodiment, stable compositions comprising an oxidizing agent comprising hydrogen peroxide, a stabilizing agent comprising urea and water. The compositions further may include an additional oxidizing compound comprising a peroxycarboxylic acid, a carboxylic acid, an additional stabilizing agent, an acid additive, and/or additional functional ingredients.

The present disclosure further provides stabilized peroxide-containing compositions without the use of pyridine carboxylic acids such as DPA. The stabilizing agent comprising urea alone effectively stabilizes various concentrations of peroxides and peroxycarboxylic acids without the use of conventional peracid stabilizers. In additional embodiments, an additional stabilizing agent comprising a chelator stabilizing agent, such as HEDP, may be used in addition to urea for providing synergistic stabilizing activity. The combination of urea and HEDP allows for reduced concentrations of HEDP while providing effective to be included in the compositions for stabilization of the oxidizing compound.

Furthermore, the compositions of the present disclosure are biodegradable, and beneficially decompose into non-hazardous products. The compositions of the present disclosure are therefore beneficial for use in direct or incidental food/feed contact and comprise only GRAS materials, or minimizes non-GRAS materials.

According to an embodiment of the disclosure the stabilized peroxycarboxylic acid compositions are suitable for storage at ambient temperatures that might occasionally reach about 50° C. In an aspect, the stabilized composition retains at least about 80% of the hydrogen peroxide and/or peroxycarboxylic acid activity after storage of up to one year at room temperature. Preferably, the methods include retaining at least about 85%, at least about 90%, or at least about 95% or higher of the oxidizing compound concentration after storage of about up to one year at room temperature. In another aspect, the stabilized composition retains at least 80% of the oxidizing compound concentration after storage of 4 weeks at a temperature of about 40° C.

In an aspect, the compositions include concentrated equilibrium compositions comprising a stabilizing agent comprising urea, an oxidizing compound comprising hydrogen peroxide, a solvent, e.g., water, and optional additional ingredients comprising additional stabilizing agents, acid additive, and additional functional ingredients (e.g., surfactants, defoaming agents, antimicrobial agents, bleaching agents, etc.). In another aspect, the compositions include concentrated equilibrium compositions comprising a stabilizing agent comprising urea, oxidizing compounds comprising carboxylic acid, peroxycarboxylic acid, and hydrogen peroxide, a solvent (e.g., water), and optional additional ingredients comprising additional stabilizing agents, acid additive, and additional functional ingredients (e.g., surfactants, defoaming agents, antimicrobial agents, bleaching agents, etc.).

In an aspect, the compositions include the exemplary ranges shown in Tables 1A and 1B in weight percentage of the concentrated equilibrium peroxide-containing compositions.

TABLE 1A

| Composition | First Exemplary Range (wt-%) | Second Exemplary Range (wt-%) | Third Exemplary Range (wt-%) | Fourth Exemplary Range (wt-%) |
|---|---|---|---|---|
| Solvent (e.g., Water) | 1-70 | 1-60 | 10-60 | 10-50 |
| Oxidizing compound (e.g., Hydrogen peroxide at 100% active levels) | 1-50 | 1-35 | 15-35 | 24-34 |
| Urea stabilizing agent | 0.01-5 | 0.1-3 | 0.5-3 | 0.5-1 |
| Additional stabilizing agent and/or Acid Additive | 0-15 | 0.01-10 | 0.1-5 | 0.1-5 |
| Additional Functional Ingredients (e.g., surfactants) | 0-60 | 0.01-50 | 0.1-5 | 0.1-40 |

TABLE 1B

| Composition | First Exemplary Range (wt-%) | Second Exemplary Range (wt-%) | Third Exemplary Range (wt-%) |
|---|---|---|---|
| Solvent (e.g., Water) | 1-50 | 1-40 | 1-30 |
| Hydrogen peroxide (at 100% actives) | 1-50 | 1-35 | 1-25 |
| Carboxylic acid | 1-90 | 1-75 | 1-70 |
| Peroxycarboxylic acid | 3-25 | 5-20 | 10-18 |
| Urea stabilizing agent | 0.01-3 | 0.1-2 | 0.1-1 |
| Additional stabilizing agent and/or Acid additive | 0-10 | 0.01-10 | 0.1-5 |
| Additional Functional Ingredients (e.g., surfactants) | 0-60 | 0.01-50 | 0.1-40 |

In yet other aspects, the compositions according to the disclosure may include non-equilibrium peroxide-containing compositions, such as where a peroxycarboxylic acid is generated in situ and/or on site through a process by one or more composition (e.g., one or more-part systems) comprising individual reagents combined according to the disclosure. In an exemplary aspect, these reagents are described herein individually along and include at least one ester of a polyhydric alcohol and a C1 to C22 carboxylic acid, an oxidizing agent, a source of alkalinity, solvents, and other functional groups/agents. An acidulant is also described herein as a reagent to be added to the compositions after the formation of the percarboxylic acid(s). Alternatively, as described herein, there may be benefits to providing the reagents in various premix formulations to decrease the number of reagents and/or increase the simplicity of the disclosure for generating peroxycarboxylic acid compositions for a particular use. Premix formulations suitable for use according to the disclosure may comprise, consist of and/or consist essentially of at least one ester of a polyhydric alcohol and a C1 to C22 carboxylic acid, an oxidizing agent, a solvent and mixtures thereof. Premix formulations suitable for use according to the disclosure may also comprise, consist of and/or consist essentially of at least one ester, an oxidizing agent, water, solvents, dispersing agents, surfactants, defoamers and mixtures thereof.

In an embodiment, the composition is provided as a dilutable liquid concentrate having an acidic pH. The dilutable liquid concentrates may be provided as a concentrated equilibrium composition, which may be diluted to form a use solution. In other embodiments, the compositions, whether generated in situ or on site from one or more premix compositions or whether provided in a concentrated equilibrium composition, in a use solution, have a pH at about 6 or less. Preferably, the compositions in a use solution have a pH at about 5 or less. In an aspect, the use solutions of the stabilized peroxide-containing compositions, when diluted pursuant to EPA sanitizer suspension preparations (e.g., dilute 1 oz. of the peroxide-containing composition to 8 Gallon with 500 ppm hard water), such that the pH of the solution is less than about 4, preferably between about 3 to about 4.

Stabilizing Agent

A stabilizing agent or agents included in compositions includes at least one urea source or urea chelator combination. Beneficially, the urea stabilizing agent prevents the decomposition of peroxide and/or peroxycarboxylic acid in an equilibrium composition. As a food ingredient, the use of urea further maintains compositions that are safe to utilize in the food and beverage sector.

The particle size of the urea is effective to combine with the additional ingredients in the composition of the present disclosure to form a homogenous mixture. The urea may be in the form of prilled beads or powder. Prilled urea is generally available from commercial sources as a mixture of particle sizes ranging from about 8-15 U.S. mesh. The amount of urea included in the composition is effective to stabilize the oxidizing compound.

The urea source is included in a concentrated equilibrium peroxide-containing composition in an amount of from about 0.01 wt-% to about 5 wt-%, from about 0.1 wt-% to about 3 wt-%, from about 0.1 wt-% to about 2 wt-%, or from about 0.1 wt-% to about 1 wt-%. Without limiting the scope of the present disclosure, the numeric ranges are inclusive of the numbers defining the range and include each integer within the defined range.

In a further embodiment, the stabilizing agent may be combined with additional conventional stabilizing agents, e.g., a chelator stabilizer such as a phosphonate-based stabilizer, to beneficially provide further increase in stability of the composition, and in some aspects, provide synergistic stabilization of the oxidizing compounds. Exemplary additional stabilizers include phosphoric acid and salts, pyrophosphoric acid and salts and most commonly, 1-hydroxyethylidene-1,1-diphosphonic acid (HEDP) and salts. When additional stabilizing agents are included, the compositions of the present disclosure incorporating urea as a stabilizing agent, beneficially reduce the amount of additional stabilizing agent(s) needed to stabilize the peroxide-containing acid composition.

In embodiments, the combination of urea and a chelator stabilizer can reduce the concentration of chelator stabilizer included in the compositions while maintaining stability of the peroxide-containing compositions. The inclusion of urea can reduce the concentration of additional stabilizing agents utilized, while still present in amounts sufficient to provide the intended stabilizing benefits to the peroxide-containing compositions. In some embodiments, the addition of the urea stabilizing agent can reduce the amount of additional stabilizing agent in the composition by at least about 30%. In other embodiments, the addition of the urea stabilizing agent can reduce the amount of additional stabilizing agent in the composition by at least 40%. In further embodiments, the addition of the urea stabilizing agent can reduce the amount of additional stabilizing agent in the composition by at least 50%.

In embodiments, the additional stabilizer comprises HEDP and salts thereof, and are included in amounts from about 0.001 wt-% to 3 wt-%, preferably from 0.001 wt-% to 2 wt-%, and more preferably from about 0.01 wt-% to about 1 wt-%. Without limiting the scope of the disclosure, the numeric ranges are inclusive of the numbers defining the range and include each integer within the defined range.

In further embodiments, the synergy between the urea stabilizing agent and HEDP reduces the amount of HEDP included in the composition to less than 34 ppm in use solution, preferably less than 15 ppm in use solution, and more preferably less than 10 ppm. Without limiting the scope of the disclosure, the numeric ranges are inclusive of the numbers defining the range and include each integer within the defined range.

In a preferred aspect, the peroxide-containing compositions are substantially free of pyridine carboxylic acids. The pyridine carboxylic acids that may be excluded from the present disclosure include dipicolinic acids, including for example, 2,6-pyridinedicarboxylic acid (DPA). In a further aspect, the excluded stabilizing agent is a picolinic acid, or a salt thereof. In an aspect, the excluded stabilizing agent is a picolinic acid or a compound having the following Formula (IA):

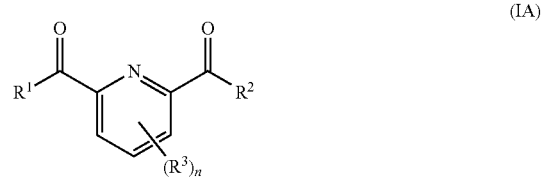

(IA)

wherein $R^1$ is OH or $-NR^{1a}R^{1b}$, wherein $R^{1a}$ and $R^{1b}$ are independently hydrogen or $(C_1-C_6)$ alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof.

In a further aspect, the excluded stabilizing agent is a compound having the following Formula (IB):

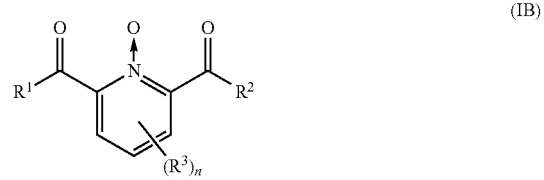

(IB)

wherein $R^1$ is OH or $-NR^{1a}R^{1b}$, wherein $R^{1a}$ and $R^{1b}$ are independently hydrogen or $(C_1-C_6)$ alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof.

Without being limited to a particular theory or mechanism, the inclusion of urea provides similar functionality to DPA with respect to stabilization of oxidizing compounds such as peroxides and peroxycarboxylic acids. Therefore, for purposes of reducing costs of raw materials, the compositions of the present disclosure may be substantially free of DPA.

Such additional stabilizing agents may be present in a concentrated equilibrium peroxide-containing composition in amounts from about 0 wt-% to about 3 wt-%, 0.01 wt-% to about 2 wt-%, and more preferably from about 0.01 wt-% to about 1 wt-%. Without limiting the scope of the disclosure, the numeric ranges are inclusive of the numbers defining the range and include each integer within the defined range.

Oxidizing Compound

In an embodiment, the oxidizing compound is hydrogen peroxide. Hydrogen peroxide ($H_2O_2$) provides the advantages of having a high ratio of active oxygen because of its low molecular weight (34.014 g/mole) and being compatible with numerous substances that can be treated by methods of the disclosure because it is a weakly acidic, clear, and colorless liquid. Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and are generally innocuous to incidental contact and are environmentally friendly.

In one aspect, the oxidizing compound comprises hydrogen peroxide. In another aspect, the hydrogen peroxide is initially in an antimicrobial peroxycarboxylic acid composition in an amount effective for maintaining an equilibrium between a carboxylic acid, hydrogen peroxide, and a peroxycarboxylic acid. The amount of hydrogen peroxide should not exceed an amount that would adversely affect the antimicrobial activity of the peroxycarboxylic acid composition.

The hydrogen peroxide can be used at any suitable concentration. In embodiments, an actives % concentration of hydrogen peroxide is included in the initial formulations from about 1 wt-% to about 50 wt-%, from about 5 wt-% to about 50 wt-%, from about 1 wt-% to about 35 wt-%, from about 10 wt-% to about 35 wt-%, preferably from about 15 wt-% to about 35 wt-%, and more preferably from about 24 wt-% to about 34 wt-%. In embodiments, a weight-% concentration of hydrogen peroxide (at varying actives concentration) is included in amounts from about 1 wt-% to about 80 wt-%, from about 1 wt-% to about 70 wt-%, from about 20 wt-% to about 70 wt-%, or from about 30 wt-% to about 70 wt-%, or still further from about 1 wt-% to about 70 wt-%, from about 1 wt-% to about 50 wt-%, or from about 1 wt-% to about 35 wt-%. Without limiting the scope of disclosure, the numeric ranges are inclusive of the numbers defining the range and include each integer within the defined range.

In some embodiments, a concentrated equilibrium composition has a concentration of hydrogen peroxide from about 0.5 wt-% to about 90 wt-%, preferably from about 1 wt-% to about 70 wt-%, and more preferably from about 1 wt-% to about 50 wt-%. Without limiting the scope of the disclosure, the numeric ranges are inclusive of the numbers defining the range and include each integer within the defined range.

In other embodiments, the oxidizing compound is a peroxycarboxylic acid. A peroxycarboxylic acid (i.e., peracid) includes a corresponding carboxylic acid and hydrogen peroxide. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid" and "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Pat. No. 8,344,026, and U.S. Patent Publication Nos. 2010/0048730 and 2012/0052134, each of which are incorporated herein by reference in their entirety. As one of skill in the art appreciates, a peroxycarboxylic acid refers to an acid having the hydrogen of the hydroxyl group in carboxylic acid replaced by a hydroxy group. Oxidizing peroxycarboxylic acids may also be referred to herein as peroxycarboxylic acids.

A peroxycarboxylic acid includes any compound of the formula $R-(COOOH)_n$, in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Preferably, a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like.

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur, or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

According to the disclosure, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

According to the disclosure, aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyacetic acid. In another embodiment, a peroxycarboxylic acid has R that is an alkyl of 1-22 carbon atoms substituted with a hydroxyl group or other polar substituent such that the substituent improves the water solubility. Methods of preparing peroxyacetic acid are known to those of skill in the art including those disclosed in U.S. Pat. No. 2,833,813, which is herein incorporated herein by reference in its entirety.

In another embodiment, a sulfoperoxycarboxylic acid has the following formula:

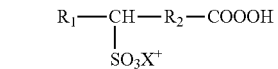

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In some embodiments, $R_1$ is a substituted or unsubstituted $C_m$ alkyl group; X is hydrogen a cationic group, or an ester forming moiety; $R_2$ is a substituted or unsubstituted $C_n$ alkyl group; m=1 to 10; n=1 to 10; and m+n is less than 18, or salts, esters, or mixtures thereof.

In some embodiments, $R_1$ is hydrogen. In other embodiments, $R_1$ is a substituted or unsubstituted alkyl group. In some embodiments, $R_1$ is a substituted or unsubstituted alkyl group that does not include a cyclic alkyl group. In some embodiments, $R_1$ is a substituted alkyl group. In some embodiments, $R_1$ is an unsubstituted $C_1$-$C_9$ alkyl group. In some embodiments, $R_1$ is an unsubstituted $C_7$ or $C_8$ alkyl. In other embodiments, $R_1$ is a substituted $C_8$-$C_{10}$ alkylene group. In some embodiments, $R_1$ is a substituted $C_8$-$C_{10}$ alkyl group is substituted with at least 1, or at least 2 hydroxyl groups. In still yet other embodiments, $R_1$ is a substituted $C_1$-$C_9$ alkyl group. In some embodiments, $R_1$ is a substituted $C_1$-$C_9$ substituted alkyl group is substituted with at least 1 $SO_3H$ group. In other embodiments, $R_1$ is a $C_9$-$C_{10}$ substituted alkyl group. In some embodiments, $R_1$ is a substituted $C_9$-$C_{10}$ alkyl group wherein at least two of the carbons on the carbon backbone form a heterocyclic group. In some embodiments, the heterocyclic group is an epoxide group.

In some embodiments, $R_2$ is a substituted $C_1$-$C_{10}$ alkylene group. In some embodiments, $R_2$ is a substituted $C_8$-$C_{10}$ alkylene. In some embodiments, $R_2$ is an unsubstituted $C_6$-$C_9$ alkylene. In other embodiments, $R_2$ is a $C_8$-$C_{10}$ alkylene group substituted with at least one hydroxyl group. In some embodiments, $R_2$ is a $C_{10}$ alkylene group substituted with at least two hydroxyl groups. In other embodiments, $R_2$ is a $C_8$ alkylene group substituted with at least one $SO_3H$ group. In some embodiments, $R_2$ is a substituted $C_9$ group, wherein at least two of the carbons on the carbon backbone form a heterocyclic group. In some embodiments, the heterocyclic group is an epoxide group. In some embodiments, $R_1$ is a $C_8$-$C_9$ substituted or unsubstituted alkyl, and $R_2$ is a $C_7$-$C_8$ substituted or unsubstituted alkylene.

In additional embodiments, mixed peroxycarboxylic acid compositions may be employed. Mixed peroxycarboxylic acid compositions comprise a sulfoperoxycarboxylic acid, a tertiary peroxycarboxylic acid, a hydrophilic peroxycarboxylic acid such as peroxyacetic acid, a hydrophobic peroxycarboxylic acid such as peroxyoctanoic acid, or a combination thereof. The mixed peroxycarboxylic acid compositions often provide synergistic micro efficacy. Accordingly, compositions of the disclosure can include a peroxycarboxylic acid, or mixtures thereof.

Various commercial formulations of peroxycarboxylic acids are available, including for example peracetic acid (approximately 15%) available as EnviroSan (Ecolab, Inc., St. Paul MN). Most commercial peroxycarboxylic acid solutions state a specific percarboxylic acid concentration without reference to the other chemical components in a use solution. However, it should be understood that commercial products, such as peracetic acid, will also contain the corresponding carboxylic acid (e.g., acetic acid), hydrogen peroxide and water.

In an aspect, any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In embodiments, a composition of the disclosure includes peroxyacetic acid, peroxyoctanoic acid, peroxypropionic acid, peroxylactic acid, peroxyheptanoic acid, peroxyoctanoic acid and/or peroxynonanoic acid. In still other embodiments, the $C_1$-$C_{22}$ percarboxylic acid comprises peroxyacetic acid, peroxyoctanoic acid and/or peroxysulfonated oleic acid.

In an aspect, a peroxycarboxylic acid may be selected from a concentrated composition having a ratio of hydrogen peroxide to peroxycarboxylic acid from about 0.5:10 to about 10:0.5, preferably from about 1:10 to about 10:1, preferably from about 1:8 to 8:1. Various concentrated peroxycarboxylic acid compositions having the hydrogen peroxide to peroxycarboxylic acid ratios of about 0.5:10 to about 10:0.5, preferably from about 1:8 to 8:1, may be employed to produce a use solution for treatment according to the methods of the disclosure. Without limiting the scope of the disclosure, the numeric ranges are inclusive of the numbers defining the range and include each integer within the defined range.

In a preferred aspect, the $C_1$-$C_{22}$ peroxycarboxylic acid can be used at any suitable concentration. In some embodiments, the $C_1$-$C_{22}$ percarboxylic acid has a concentration from about 0.1 wt-% to about 40 wt-% in a concentrated equilibrium composition. In other embodiments, the $C_1$-$C_{22}$ percarboxylic acid has a concentration from about 1 wt-% to about 35 wt-%, from about 1 wt-% to about 30 wt-%, from about 1 wt-% to about 25 wt-%, from about 3 wt-% to about 25 wt-%, from about 5 wt-% to about 20 wt-%, or from about 10 wt-% to about 18 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%. Without limiting the scope of disclosure, the numeric ranges are inclusive of the numbers defining the range and include each integer within the defined range.

In embodiments, the oxidizing compound comprises any peroxide forming compound. In other embodiments, the oxidizing compound comprises hydrogen peroxide, peroxycarboxylic acid, or a combination thereof. In additional embodiments, the oxidizing compound consists of hydrogen peroxide and peroxycarboxylic acid. In embodiments, the peroxide-containing compositions are substantially free of oxidizing compounds comprising nitric oxides or nitrate containing oxidizing compounds.

Carboxylic Acid

The present disclosure may include a carboxylic acid with the hydrogen peroxide. A carboxylic acid includes any compound of the formula R—(COOH)$_n$, in which R can be hydrogen, alkyl, alkenyl, alkyne, acylic, alicyclic group, aryl, heteroaryl, or heterocyclic group, and n is 1, 2, or 3. Preferably R includes hydrogen, alkyl, or alkenyl. The terms "alkyl," "alkenyl," "alkyne," "acylic," "alicyclic group," "aryl," "heteroaryl," and "heterocyclic group" are as defined above with respect to peroxycarboxylic acids.

Examples of suitable carboxylic acids according to the equilibrium systems of peroxycarboxylic acids according to the disclosure include a variety monocarboxylic acids, dicarboxylic acids, and tricarboxylic acids. Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc. Dicarboxylic acids include, for example, adipic acid, fumaric acid, glutaric acid, maleic acid, succinic acid, malic acid, tartaric acid, etc. Tricarboxylic acids include, for example, citric acid, trimellitic acid, isocitric acid, agaicic acid, etc.

In an aspect, a particularly well-suited carboxylic acid is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. Preferably a composition of the disclosure includes acetic acid, octanoic acid, or propionic acid, lactic acid, heptanoic acid, octanoic acid, or nonanoic acid. In a preferred embodiment, the carboxylic acid is acetic acid. In a further embodiment, the carboxylic acid is acetic acid and octanoic acid. Additional examples of suitable carboxylic acids are employed in sulfoperoxycarboxylic acid or sulfonated peroxycarboxylic acid systems, which are disclosed in U.S. Pat. No. 8,344,026, and U.S. Patent Publication Nos. 2010/0048730 and 2012/0052134, each of which are herein incorporated by reference in their entirety.

Any suitable $C_1$-$C_{22}$ carboxylic acid can be used in the present compositions. In some embodiments, the $C_1$-$C_{22}$ carboxylic acid is a $C_2$-$C_{20}$ carboxylic acid. In other embodiments, the $C_1$-$C_{22}$ carboxylic acid is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ carboxylic acid comprises acetic acid, octanoic acid and/or sulfonated oleic acid.

The $C_1$-$C_{22}$ carboxylic acid can be used at any suitable concentration. In some embodiments, the $C_1$-$C_{22}$ carboxylic acid has an initial formulation concentration from about 0.1 wt-% to about 90 wt-%. In other embodiments, the $C_1$-$C_{22}$ carboxylic acid has a concentration from about 1 wt-% to about 80 wt-%, or from about 1 wt-% to about 75 wt-%. In still other embodiments, the $C_1$-$C_{22}$ carboxylic acid has a concentration at about 1 wt-% to about 70 wt-%, or from about 5 wt-% to about 60 wt-%. Without limiting the scope of disclosure, the numeric ranges are inclusive of the numbers defining the range and include each integer within the defined range.

Acid Additives

In some embodiments, the present composition may further include one or more acid additives. In some aspects, the peroxide-containing composition has a use solution pH of 5 or less, and preferably has a use solution pH of 4 or less. The presence of acid additives in the present composition serves as a catalyst to drive the reaction of the composition to equilibrium. In embodiments, the present composition includes an inorganic acid, an organic acid, or a combination thereof. In preferred embodiments, the present composition includes a mineral acid.

Particularly suitable acids include phosphoric acid ($H_3PO_4$), sodium hydrogen sulfate, nitric acid, and sulfonic acids both alkyl and aryl, in particular methane sulfonic acid and dodecylbenzene, toluene, xylene, naphthalene and cumene sulfonic acid, and/or sulfuric acid ($H_2SO_4$). Additional phosphonic acids which may be used according to the disclosure include, for example, aminotrimethylene phosphonic acid, ethylene diamine tetramethylene phosphonic acid, hexamethylene diamine tetramethylene phosphonic acid, and/or diethylene triamine tetramethylene phosphonic acid. Additional description of mineral acids for use in peroxycarboxylic acid compositions is disclosed in WO 91/07375, which is herein incorporated by reference in its entirety.

The acid additives serving as a catalyst for the peroxide-containing compositions can be used at any suitable concentration. In some embodiments the role of the acid additive can be provided by an additional stabilizing agent that is also a strong acid (e.g., HEDP) to drive a reaction as there is a suitable concentration of acid, e.g., from a peroxycarboxylic acid composition or a peroxycarboxylic acid generating composition. In some embodiments, the initial formulation concentration of the acid, in active %, is present in an amount of from about 0.01 wt-% to about 20 wt-%, or from about 0.1 wt-% to about 10 wt-%. In still other embodiments, the acid has a concentration from about 0.1 wt-% to about 8 wt-%, or more preferably from about 0.1 wt-% to about 5 wt-%. Without limiting the scope of disclosure, the numeric ranges are inclusive of the numbers defining the range and include each integer within the defined range.

Additional Functional Ingredients

In some embodiments, the present composition can further comprise additional functional ingredients. In some embodiments, the composition including the hydrogen peroxide, urea, water, and optional peroxycarboxylic acid and acid additive make up a large amount, or even substantially all of the total weight of the compositions. For example, in some embodiments few or no additional functional ingredients are disposed therein.

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used. In some aspects, the compositions may include defoaming agents, surfactants, additional antimicrobial agents, anti-redeposition agents, bleaching agents, solubility modifiers, dispersants, rinse aids, metal protecting agents, stabilizing agents, corrosion inhibitors, fragrances and/or dyes, rheology modifiers or thickeners, hydrotropes or couplers, buffers, solvents, and the like.

In preferred embodiments, the compositions further include substances that aid in the solubilization of the stabilizing agent(s), including for example, hydrotropes such as sodium xylene sulfonate (SXS), sodium cumene sulfonates (SCS), surfactants, such as anionic surfactants and nonionic surfactants, and a defoaming agent. In further aspects, the composition may utilize alternative hydrotropes for solubilization of the stabilizing agent, including for example, n-octanesulfonate, a xylene sulfonate, a naphthalene sulfonate, ethylhexyl sulfate, lauryl sulfate, an amine oxide, etc.

In some embodiments, the compositions include about 0 wt-% to about 60 wt-% of additional functional ingredients. In other embodiments the compositions include about 0.01 wt-% to about 50 wt-% of additional functional ingredients, preferably from about 0.1 wt-% to about 45 wt-% of additional functional ingredients, and more preferably from about 0.1 wt-% to about 40 wt-% of additional functional ingredients.

Surfactants

In some embodiments, the compositions may include a surfactant. Surfactants suitable for use with the peroxide-containing compositions include, but are not limited to, nonionic surfactants and/or anionic surfactants. Preferably, a low foaming anionic surfactant is included in the peroxycarboxylic acid compositions. Beneficially, according to embodiments, the use of the defoaming agent (e.g., aluminum sulfate) in combination with the surfactant overcomes the foaming issues that are known to result from the use of conventional low-foaming surfactants in peroxycarboxylic acid compositions, especially in deionized or soft water.

Anionic Surfactants

Preferably, surface active substances which are categorized as anionics because the charge on the hydrophobe is negative are utilized; or surfactants in which the hydrophobic section of the molecule carries no charge unless the pH is elevated to neutrality or above (e.g., carboxylic acids). Carboxylate, sulfonate, sulfate, and phosphate are the polar (hydrophilic) solubilizing groups found in anionic surfactants. Of the cations (counter ions) associated with these polar groups, sodium, lithium, and potassium impart water solubility; ammonium and substituted ammonium ions provide both water and oil solubility; and calcium, barium, and magnesium promote oil solubility. As those skilled in the art understand, anionics are excellent detersive surfactants and are therefore favored additions to heavy duty detergent compositions.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g., alkyl succinates), ether carboxylic acids, sulfonated fatty acids, such as sulfonated oleic acid, and the like. Such carboxylates include alkyl ethoxy carboxylates, alkyl aryl ethoxy carboxylates, alkyl polyethoxy polycarboxylate surfactants and soaps (e.g., alkyl carboxyls). Secondary carboxylates useful in the present compositions include those which contain a carboxyl unit connected to a secondary carbon. The secondary carbon can be in a ring structure, e.g., as in p-octyl benzoic acid, or as in alkyl-substituted cyclohexyl carboxylates. The secondary carboxylate surfactants typically contain no ether linkages, no ester linkages, and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acyl glutamates, acyl peptides, sarcosinates (e.g., N-acyl sarcosinates), taurates (e.g., N-acyl taurates and fatty acid amides of methyl tauride), and the like.

Suitable anionic surfactants include alkyl or alkylaryl ethoxy carboxylates of the following formula:

$$R-O-(CH_2CH_2O)_n(CH_2)_m-CO_2X \qquad (3)$$

in which R is a $C_8$ to $C_{22}$ alkyl group or

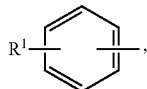

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

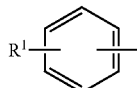

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g., the product Sandopan® DTC, a $C_{13}$ alkyl polyethoxy (7) carboxylic acid.

Nonionic Surfactants

Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water-soluble compound having the desired degree of balance between hydrophilic and hydrophobic properties. Useful nonionic surfactants include:

Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp. Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Tetronic® compounds are tetra-functional block copolymers derived from the sequential addition of propylene oxide and ethylene oxide to ethylenediamine. The molecular weight of the propylene oxide hydrotype ranges from about 500 to about 7,000; and the hydrophile, ethylene oxide, is added to constitute from about 10% by weight to about 80% by weight of the molecule.

Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

Condensation products of one mole of a saturated or unsaturated, straight, or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol™ manufactured by Shell Chemical Co. and Alfonic™ manufactured by Vista Chemical Co.

Condensation products of one mole of saturated or unsaturated, straight, or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol™ manufactured by Henkel Corporation and Lipopeg™ manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in the present application for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty esters or acylated carbohydrates to compositions containing amylase and/or lipase enzymes because of potential incompatibility.

Examples of nonionic low foaming surfactants include:

Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics™ are manufactured by BASF Corporation under the trade name Pluronic™ R surfactants. Likewise, the Tetronic™ R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

The alkylphenoxypolyethoxyalkanols of U.S. Pat. No. 2,903,486 issued Sep. 8, 1959 to Brown et al. and represented by the formula

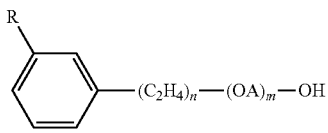

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n(C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6O)_n(C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the peroxide-containing compositions correspond to the formula: $P[(C_3H_6O)_n (C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

Polyhydroxy fatty acid amide surfactants suitable for use in the present compositions include those having the structural formula $R_2CON_{R1}Z$ in which: R1 is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_6$-$C_{18}$ ethoxylated fatty alcohols with a degree of ethoxylation of from 3 to 50.

Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Fatty acid amide surfactants suitable for use the present compositions include those having the formula: $R_6CON(R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or $—(C_2H_4O)_xH$, where x is in the range of from 1 to 3.

A useful class of non-ionic surfactants include the class defined as alkoxylated amines or, most particularly, alcohol alkoxylated/aminated/alkoxylated surfactants. These non-ionic surfactants may be at least in part represented by the general formulae: $R^{20}—(PO)_sN-(EO)_tH$, $R^{20}—(PO)_sN-(EO)_tH(EO)_zH$, and $R^{20}—N(EO)_tH$; in which $R^{21}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: $R^{20}—(PO)_v—N[(EO)_wH][(EO)_zH]$ in which $R^{20}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes Surfonic™ PEA 25 Amine Alkoxylate. Preferred nonionic surfactants for the peroxide-containing compositions include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present application. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Semi-Polar Nonionic Surfactants

The semi-polar type of nonionic surface-active agents are another class of nonionic surfactant useful in the peroxide-containing compositions. Generally, semi-polar nonionics are high foamers and foam stabilizers, which can limit their application in clean-in-place (CIP) systems. However, within compositional embodiments designed for high foam cleaning methodology, semi-polar nonionics would have immediate utility. The semi-polar nonionic surfactants include the amine oxides, phosphine oxides, sulfoxides and their alkoxylated derivatives.

Amine oxides are tertiary amine oxides corresponding to the general formula:

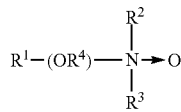

wherein the arrow is a conventional representation of a semi-polar bond; and $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g., through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water-soluble phosphine oxides having the following structure:

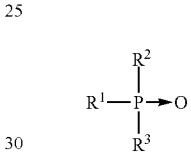

wherein the arrow is a conventional representation of a semi-polar bond; and $R^1$ is an alkyl, alkenyl or hydroxyalkyl moiety ranging from 10 to about 24 carbon atoms in chain length; and $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide. Semi-polar nonionic surfactants useful herein also include the water-soluble sulfoxide compounds which have the structure:

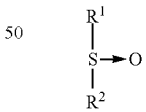

wherein the arrow is a conventional representation of a semi-polar bond; and $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the peroxide-containing compositions include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Suitable nonionic surfactants suitable for use with the peroxide-containing compositions include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like.

Methods of Delivery and Methods of Use

In an aspect, the present disclosure is directed to a method of stabilizing a peroxide-containing composition. The method involves combining a stabilizing agent comprising urea, with an oxidizing compound. In an embodiment, the stabilization of the peroxide-containing composition includes storing the compositions, wherein at least about 80% of the oxidizing compound concentration is retained after storage for any suitable time under any suitable conditions, e.g., retaining at least about 80% of the hydrogen peroxide and/or peroxycarboxylic acid activity after storage of about 4 weeks at about 40° C., or after storage of up to one year at room temperature. Preferably, the methods include retaining at least about 85%, at least about 90%, or at least about 95% or higher of the oxidizing compound concentration after storage of about 4 weeks at about 40° C., or after storage of up to one year at room temperature.

In still another aspect, the present disclosure includes use of the compositions for sanitizing or cleaning surfaces and/or products. In another aspect, the compositions of the disclosure are particularly suitable for use as a hard surface sanitizer and/or disinfectant, a CIP sanitizer, food and/or tissue treatment sanitizer (including direct or indirect contact sanitizer), an environmental disinfectant, a laundry bleach and disinfectant, and/or an indirect food contact sanitizer. The present methods can be used in the methods, processes or procedures described and/or claimed in U.S. Pat. Nos. 5,200,189, 5,314,687, 5,718,910, 6,165,483, 6,238,685B1, 8,017,409 and 8,236,573, each of which are herein incorporated by reference in their entirety.

The compositions are particularly suitable for direct or indirect contact sanitizer for a food item or a plant item and/or at least a portion of a medium, a container, an equipment, a system, or a facility for growing, holding, processing, packaging, storing, transporting, preparing, cooking, or serving the food item or the plant item. The present methods can be used for treating any suitable plant item. In some embodiments, the plant item is a grain, fruit, vegetable or flower plant item, a living plant item or a harvested plant item, and/or animal feed. In addition, the present methods can be used for treating any suitable food item, e.g., an animal product, an animal carcass or an egg, a fruit item, a vegetable item, or a grain item. In still other embodiments, the food item may include a fruit, grain and/or vegetable item.

The present methods can be used for treating a target that is at least a portion of a container, an equipment, a system, or a facility for holding, processing, packaging, storing, transporting, preparing, cooking, or serving the food item or the plant item. In some embodiments, the target is at least a portion of a container, an equipment, a system, or a facility for holding, processing, packaging, storing, transporting, preparing, cooking, or serving a meat item, a fruit item, a vegetable item, or a grain item. In other embodiments, the target is at least a portion of a container, an equipment, a system, or a facility for holding, processing, packaging, storing, or transporting an animal carcass. In still other embodiments, the target is at least a portion of a container, an equipment, a system, or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The present methods can be used for treating a target that is at least a portion of a solid surface or liquid media. In some embodiments, the solid surface is an inanimate solid surface. The inanimate solid surface can be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment, or the surface of a fabric.

In still another aspect, the present disclosure includes water treatment methods and other industrial processes uses of the compositions for sanitizing surfaces and/or products. In some aspects, the disclosure includes methods of using urea to stabilize peroxide and/or peroxycarboxylic acid compositions to prevent biological fouling in various industrial processes and industries, including oil and gas operations, to control microorganism growth, eliminate microbial contamination, limit, or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid compositions are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this disclosure could be applied are in process water applications (flume water, shower water, washers, thermal processing waters, brewing, fermentation, CIP (clean in place), hard surface sanitization, etc.), Ethanol/Bio-fuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields—oil and gas wells/flow line, water systems, gas systems, etc.), and in particular water systems where the installed process equipment exhibits lowered compatibility to halogenated biocides.

The methods by which the peroxide-containing compositions are introduced into the aqueous fluids or liquid systems are not critical. Introduction of the peroxide-containing compositions may be carried out in a continuous or intermittent manner and will depend on the type of water and/or liquid being treated. In some embodiments, the compositions are introduced into an aqueous fluid according to the methods disclosed in U.S. patent application Ser. No. 13/645,671, titled "New Method and Arrangement for Feeding Chemicals into a Hydrofracturing Process and Oil and Gas Applications", which is hereby incorporated by reference in its entirety.

Those skilled in the art will recognize or be able to ascertain using no more than routine experimentation, numerous equivalents to the specific procedures, embodiments, claims, and examples described herein. Such equivalents are considered to be within the scope of this disclosure and covered by the claims appended hereto. The contents of all references, patents, and patent applications cited throughout this application are hereby incorporated by reference to the same extent as if each individual publication or patent application were specifically and individually indicated as incorporated by reference. All publications and patent applications in this specification are indicative of the level of ordinary skill in the art to which this disclosure pertains. The disclosure is further illustrated by the following examples, which should not be construed as further limiting.

The various applications of use described herein provide the peroxide-containing compositions to a surface, liquid and/or product in need of antimicrobial and/or sanitizing treatment. Beneficially, the compositions of the disclosure are fast-acting. However, the present methods require a certain minimal contact time of the compositions with the surface, liquid and/or product in need of treatment for occurrence of sufficient antimicrobial effect. The contact time can vary with concentration of the use compositions, method of applying the use compositions, temperature of the use compositions, pH of the use compositions, amount of the surface, liquid and/or product to be treated, amount of soil or substrates on/in the surface, liquid and/or product to be treated, or the like. The contact or exposure time can be at least about 15 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. In other embodiments, the exposure time is a few hours to days. The contact time will further vary based upon the concentration of oxidizing compound in a use solution.

The present methods can be conducted at any suitable temperature. In some embodiments, the present methods are conducted at a temperature ranging from about 0° C. to about 70° C., e.g., from about 0° C. to about 4° C. or 5° C., from about 5° C. to about 10° C., from about 11° C. to about 20° C., from about 21° C. to about 30° C., from about 31° C. to about 40° C., including at about 37° C., from about 41° C. to about 50° C., from about 51° C. to about 60° C., or from about 61° C. to about 70° C.

In embodiments, the compositions comprising peroxycarboxylic acid are suitable for antimicrobial efficacy against a broad spectrum of microorganisms, providing broad spectrum bactericidal and fungistatic activity. For example, the peroxycarboxylic acid biocides of this disclosure provide broad spectrum activity against wide range of different types of microorganisms (including both aerobic and anaerobic microorganisms), including bacteria, yeasts, molds, fungi, algae, and other problematic microorganisms.

The present methods can be used to achieve any suitable reduction of the microbial population in and/or on the target or the treated target composition. In some embodiments, the present methods can be used to reduce the microbial population in and/or on the target or the treated target composition by at least one $\log_{10}$. In other embodiments, the present methods can be used to reduce the microbial population in and/or on the target or the treated target composition by at least two $\log_{10}$. In still other embodiments, the present methods can be used to reduce the microbial population in and/or on the target or the treated target composition by at least three $\log_{10}$.

The peroxide-containing compositions may include concentrate compositions or may be diluted to form use compositions. In general, a concentrate refers to a composition that is intended to be diluted with water to provide a use solution that contacts a surface, liquid and/or product in need of treatment to provide the desired cleaning, sanitizing or the like. The composition that contacts the surface, liquid and/or product in need of treatment can be referred to as a concentrate or a use composition (or use solution) dependent upon the formulation employed in methods according to the disclosure. It should be understood that the concentration of the active components in the composition will vary depending on whether the composition is provided as a concentrate or as a use solution. The concentrated detergent composition may be provided, for example, in the form of a solid liquid. Preferably, the concentrated detergent composition is provided in the form of a liquid.

A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

All publications and patent applications in this specification are indicative of the level of ordinary skill in the art to which this disclosure pertains. All publications and patent applications are herein incorporated by reference to the same extent as if each individual publication or patent application were specifically and individually indicated as incorporated by reference.

EXAMPLES

Embodiments are further defined in the following non-limiting Examples. It should be understood that these Examples, while indicating certain embodiments, are given by way of illustration only. From the above discussion and these Examples, one skilled in the art can ascertain the essential characteristics of this disclosure, and without departing from the spirit and scope thereof, can make various changes and modifications of the embodiments to adapt it to various usages and conditions. Thus, various modifications of the embodiments, in addition to those shown and described herein, will be apparent to those skilled in the art from the foregoing description. Such modifications are also intended to fall within the scope of the appended claims.

Example 1

The stability of peroxide containing compositions were evaluated utilizing urea as a stabilization agent. The concentration of hydrogen peroxide ($H_2O_2$) was measured weekly at a temperature of 40° C. for 4 weeks. Testing at a temperature of 40° C. demonstrated one-year stability of the composition at room temperature. The evaluated formulations are shown in Table 2 along with the stabilization results for each formulation. The results demonstrate the concentration of hydrogen peroxide present at day 7, day 21, and day 28.

TABLE 2

| | Formulations (wt-%) | | | |
|---|---|---|---|---|
| Composition | A | B | C | D |
| DI Water | 30.0 | 29.5 | 29.0 | 29.9 |
| Hydrogen peroxide ($H_2O_2$), 50% | 68.0 | 68.0 | 68.0 | 68.0 |
| Urea (prilled) | 0.00 | 0.50 | 1.00 | 0.10 |
| Methanesulfonic acid (MSA), 70% | 2.00 | 2.00 | 2.00 | 2.00 |
| Total | 100 | 100 | 100 | 100 |
| | Concentration (wt-%) | | | |
| Day 7, $H_2O_2$, 40° C. | 33.5 | 34.0 | 33.5 | 33.5 |
| Day 14, $H_2O_2$, 40° C. | * | * | * | * |
| Day 21, $H_2O_2$, 40° C. | 32.3 | 33.9 | 33.6 | 33.5 |
| Day 28, $H_2O_2$, 40° C. | 31.6 | 35.1 | 33.8 | 34.3 |

The results demonstrate the significant benefits in maintaining peroxide stability utilizing urea as a stabilizing agent. As shown in Table 2, the formulation without urea, Formulation A, resulted in a constant decrease in hydrogen peroxide concentration from day 7 through day 28. Alternatively, the formulations containing urea maintained the concentration of hydrogen peroxide. As the concentration of the remaining components of each formulation remained the same, the effects on peroxide stability can be attributable to the presence of urea.

Example 2

Urea was further evaluated for its stabilization effects on various formulations containing both a peroxide and peroxycarboxylic acid. Similar to Example 1, the equilibrium concentration of both hydrogen peroxide and peroxyacetic acid (POAA) were evaluated over a period of 4 weeks at a temperature of 40° C. The formulations evaluated contained a higher concentration of peroxide in comparison to carboxylic acid. At equilibrium, prior to decomposition, the concentration of hydrogen peroxide was about 28 wt-% and the concentration of peroxyacetic acid was about 5 wt-%.

Various compositions were formulated utilizing methanesulfonic acid as a source of strong acid. The formulations are shown in Table 3 along with the stabilization results for each formulation. The results demonstrate the concentration of hydrogen peroxide and peroxyacetic acid present at day 14, day 21, and day 28.

TABLE 3

| | Formulation (wt-%) | | | |
|---|---|---|---|---|
| Composition | E | F | G | H |
| DI Water | 28.8 | 28.7 | 28.3 | 27.8 |
| $H_2O_2$, 50% | 60.2 | 60.2 | 60.2 | 60.2 |
| Urea (prilled) | 0.00 | 0.10 | 0.50 | 1.00 |
| MSA, 70% | 1.00 | 1.00 | 1.00 | 1.00 |
| Acetic acid, 100% | 10.0 | 10.0 | 10.0 | 10.0 |
| Total | 100 | 100 | 100 | 100 |
| | Concentration (wt-%) | | | |
| Day 14, POAA, 40° C. | 4.69 | 4.97 | 5.05 | 4.81 |
| Day 21, POAA, 40° C. | 4.28 | 5.04 | 5.04 | 5.01 |
| Day 28, POAA, 40° C. | 4.03 | 4.62 | 4.94 | 4.92 |
| Day 14, $H_2O_2$, 40° C. | 27.4 | 28.1 | 28.1 | 28.0 |
| Day 21, $H_2O_2$, 40° C. | 26.0 | 27.4 | 28.1 | 27.9 |
| Day 28, $H_2O_2$, 40° C. | 25.3 | 27.5 | 28.3 | 27.7 |

The results demonstrate the significant benefits in maintaining both peroxide and peroxycarboxylic acid stability utilizing urea as a stabilizing agent. As shown in Table 3, the formulation without urea, Formulation E, resulted in a constant decrease in both hydrogen peroxide and peroxyacetic acid concentration from day 14 through day 28. Alternatively, the formulations containing urea maintained the concentration of both hydrogen peroxide and peroxyacetic acid relatively close to equilibrium concentrations. As the concentration of the remaining components of each formulation remained the same, the effects on peroxide stability can be attributable to the presence of urea.

Various compositions were further evaluated utilizing either 1-hydroxyethylidene-1,1-diphosphonic acid (HEDP) or phosphoric acid as an acid source. The formulations are shown in Table 4 along with the stabilization results for each formulation at both 20° C. and at 40° C. The results demonstrate the concentration of hydrogen peroxide and peroxyacetic acid present at day 7, day 14, day 21, and day 28.

TABLE 4

| Composition | Formulations (wt-%) | | | | | |
|---|---|---|---|---|---|---|
| | I | J | K | L | M | N |
| DI Water | 28.8 | 28.3 | 27.8 | 29.0 | 28.5 | 28.0 |
| $H_2O_2$, 50% | 60.2 | 60.2 | 60.2 | 60.2 | 60.2 | 60.2 |
| Urea | 0.00 | 0.50 | 1.00 | 0.00 | 0.50 | 1.00 |
| HEDP, 60% | 1.00 | 1.00 | 1.00 | 0.00 | 0.00 | 0.00 |
| Phosphoric acid, 75% | 0.00 | 0.00 | 0.00 | 0.80 | 0.80 | 0.80 |
| Acetic acid, 100% | 10.0 | 10.0 | 10.0 | 10.0 | 10.0 | 10.0 |
| Total | 100 | 100 | 100 | 100 | 100 | 100 |
| Concentration (wt-%) | | | | | | |
| Day 7, POAA, 20° C. | 4.85 | 4.33 | 4.25 | 3.59 | 4.39 | 4.49 |
| Day 14, POAA, 20° C. | 5.12 | 4.82 | 4.74 | 3.62 | 4.66 | 4.76 |
| Day 21, POAA, 20° C. | 5.22 | 4.95 | 5.12 | 3.20 | 4.88 | 5.10 |
| Day 28, POAA, 20° C. | 4.97 | 4.88 | 4.70 | 2.87 | 4.91 | 4.88 |
| Day 7, $H_2O_2$, 20° C. | 28.2 | 28.0 | 28.5 | 27.1 | 28.2 | 28.1 |
| Day 14, $H_2O_2$, 20° C. | 28.6 | 27.8 | 28.1 | 25.8 | 28.1 | 28.0 |
| Day 21, $H_2O_2$, 20° C. | 27.8 | 27.5 | 27.7 | 23.3 | 27.8 | 27.7 |
| Day 28, $H_2O_2$, 20° C. | 28.1 | 28.0 | 28.2 | 22.8 | 28.1 | 28.0 |
| Day 7, POAA, 40° C. | 5.12 | 4.77 | 4.92 | 3.39 | 4.80 | 4.74 |
| Day 14, POAA, 40° C. | 4.83 | 4.90 | 4.74 | 2.86 | 4.72 | 4.85 |
| Day 21, POAA, 40° C. | 4.97 | 5.09 | 5.09 | 2.09 | 4.85 | 4.69 |
| Day 28, POAA, 40° C. | 5.10 | 5.13 | 5.05 | 1.88 | 5.24 | 4.99 |
| Day 7, $H_2O_2$, 40° C. | 28.7 | 28.2 | 28.5 | 24.7 | 28.3 | 28.1 |
| Day 14, $H_2O_2$, 40° C. | 28.6 | 28.4 | 28.7 | 22.2 | 28.4 | 28.1 |
| Day 21, $H_2O_2$, 40° C. | 29.8 | 29.0 | 28.8 | 17.3 | 28.4 | 27.8 |
| Day 28, $H_2O_2$, 40° C. | 30.0 | 29.2 | 29.2 | 16.7 | 28.8 | 28.5 |

The results demonstrate that both HEDP and urea provide significant benefits in maintaining both peroxide and peroxycarboxylic acid stability. As shown in Table 4, the formulations containing urea alone as a stabilizing agent demonstrated comparable stabilizing properties to the formulation utilizing HEDP at a concentration of about 1 wt-% without urea, Formulation L However, the formulation without either HEDP or urea, Formulation L, resulted in a drastic decrease in both hydrogen peroxide and peroxyacetic acid concentration from day 7 through day 28. The results therefore demonstrate that urea provides comparable or better stabilization than HEDP, and further demonstrates a synergistic relationship in utilizing both urea and HEDP with respect to peroxide and peroxycarboxylic acid stabilization.

Various compositions were further evaluated for peroxide and peroxycarboxylic acid stabilization utilizing phosphoric acid as an acid source, and further comparing compositions utilizing HEDP and/or urea. The formulations are shown in Table 5 along with the stabilization results for each formulation at both 20° C. and at 40° C. The results demonstrate the concentration of hydrogen peroxide and peroxyacetic acid present at day 4 or 7, day 14, day 21, and day 28.

TABLE 5

| Composition | Formulation (wt-%) | | | | | |
|---|---|---|---|---|---|---|
| | O | P | Q | R | S | T |
| DI Water | 27.8 | 27.3 | 27.2 | 26.8 | 26.3 | 27.3 |
| $H_2O_2$, 50% | 60.2 | 60.2 | 60.2 | 60.2 | 60.2 | 60.2 |
| Acetic acid, 100% | 10.0 | 10.0 | 10.0 | 10.0 | 10.0 | 10.0 |
| Urea (bead) | 0.00 | 0.00 | 0.10 | 0.50 | 1.00 | 0.50 |
| HEDP, 60% | 0.00 | 0.50 | 0.50 | 0.50 | 0.50 | 0.00 |
| Phosphoric acid, 75% | 2.00 | 2.00 | 2.00 | 2.00 | 2.00 | 2.00 |
| Total | 100 | 100 | 100 | 100 | 100 | 100 |
| Concentration (wt-%) | | | | | | |
| Day 4, POAA, 20° C. | 4.27 | 4.24 | 4.47 | 3.90 | 4.20 | 4.09 |
| Day 14, POAA, 20° C. | 4.57 | 4.40 | 5.26 | 5.05 | 5.12 | 4.98 |
| Day 21, POAA, 20° C. | 4.38 | 4.19 | 5.07 | 5.24 | 5.11 | 4.94 |
| Day 28, POAA, 20° C. | 4.14 | 3.97 | 5.13 | 5.23 | 5.11 | 4.87 |
| Day 4, $H_2O_2$, 20° C. | 28.1 | 28.2 | 28.1 | 28.9 | 28.5 | 28.2 |
| Day 14, $H_2O_2$, 20° C. | 27.1 | 27.1 | 27.9 | 28.4 | 28.1 | 27.8 |
| Day 21, $H_2O_2$, 20° C. | 28.6 | 26.4 | 27.8 | 28.5 | 28.1 | 27.8 |
| Day 28, $H_2O_2$, 20° C. | 25.7 | 25.4 | 27.7 | 28.7 | 28.1 | 27.8 |
| Day 7, POAA, 40° C. | 4.38 | 4.52 | 4.98 | 4.89 | 4.91 | 4.71 |
| Day 14, POAA, 40° C. | 4.04 | 3.73 | 4.83 | 4.93 | 4.78 | 4.64 |
| Day 21, POAA, 40° C. | 3.58 | 2.92 | 4.82 | 4.95 | 4.99 | 4.54 |
| Day 28, POAA, 40° C. | 3.26 | 2.44 | 4.74 | 4.88 | 4.89 | 4.51 |
| Day 7, $H_2O_2$, 40° C. | 27.4 | 27.5 | 27.8 | 28.4 | 28.1 | 28.1 |
| Day 14, $H_2O_2$, 40° C. | 25.6 | 24.9 | 27.9 | 28.5 | 27.7 | 27.4 |

TABLE 5-continued

| Composition | Formulation (wt-%) | | | | | |
|---|---|---|---|---|---|---|
| | O | P | Q | R | S | T |
| Day 21, $H_2O_2$, 40° C. | 23.8 | 21.7 | 27.8 | 28.4 | 27.8 | 27.2 |
| Day 28, $H_2O_2$, 40° C. | 22.6 | 19.5 | 27.4 | 28.4 | 27.9 | 26.9 |

The results demonstrate that as the concentration of urea increases when used in combination with HEDP, the stabilization effects on both hydrogen peroxide and peroxyacetic acid generally increased. This demonstrates the synergistic effects of utilizing both HEDP and urea for stabilization. As represented by Formulation O, the composition that did not include either urea or HEDP resulted in a drastic reduction in concentration of both hydrogen peroxide and peroxyacetic acid from day 4 throughout day 28 at both 20° C. and 40° C. Alternatively, as shown by Formulation T, which included urea but did not include any HEDP, the stabilization effects of utilizing urea alone resulted in comparable stabilization to the formulations containing HEDP alone, or both HEDP and urea. However, especially at higher temperatures, or at 40° C., urea demonstrated substantially better stabilization of both hydrogen peroxide and peroxyacetic acid in comparison to compositions utilizing only HEDP (i.e., Formulation P). Therefore, the results demonstrate that urea provides superior long-term stability in comparison to compositions utilizing HEDP as a stabilizing agent.

Example 3

Urea was further evaluated for its stabilization effects on various formulations containing a peroxide in combination with two different peroxycarboxylic acids. Compositions were formulated utilizing urea in addition to acetic acid and octanoic acid. Various combinations of HEDP, MSA, and phosphoric acid were utilized in the compositions. The concentration of both hydrogen peroxide and peroxyacetic acid (POAA) were evaluated over a period of 5 weeks at a temperature of both 20° C. and 40° C. The formulations evaluated contained a higher concentration of peroxycarboxylic acid in comparison to peroxide. At equilibrium, prior to decomposition, the concentration of peroxyacetic acid was about 13 wt-%, the concentration of peroxyoctanoic acid was about 1 wt-%, and the concentration of hydrogen peroxide was about 3 wt-%.

The formulations are shown in Table 6 along with the stabilization results for each formulation. The results demonstrate the concentration of hydrogen peroxide and total peroxycarboxylic acid at day 7, day 14, day 21, day 28, and day 35. It is noted that the total moles of peroxygen was measured, however, due to the varying molecular weights of the mixed peroxycarboxylic acids present, the total concentration for the peroxycarboxylic acids are reported as a wt-% calculation of total peroxyacetic acid (i.e., shown as POAA).

TABLE 6

| Composition | Formulation (wt-%) | | | | | | |
|---|---|---|---|---|---|---|---|
| | U | V | W | X | Y | Z | A1 |
| Acetic acid, 100% | 59.0 | 59.0 | 59.0 | 59.0 | 59.0 | 59.0 | 59.0 |
| Octanoic acid | 10.0 | 10.0 | 10.0 | 10.0 | 10.0 | 10.0 | 10.0 |
| DI water | 8.70 | 8.90 | 8.50 | 8.00 | 9.00 | 8.90 | 8.80 |
| $H_2O_2$, 50% | 21.0 | 21.0 | 21.0 | 21.0 | 21.0 | 21.0 | 21.0 |
| Urea (prilled) | 0.00 | 0.10 | 0.50 | 1.00 | 0.00 | 0.10 | 0.20 |
| HEDP, 60% | 0.30 | 0.00 | 0.00 | 0.00 | 1.00 | 1.00 | 0.50 |
| Phosphoric acid, 75% | 1.00 | 1.00 | 1.00 | 1.00 | 0.00 | 0.00 | 0.50 |
| Total | 100 | 100 | 100 | 100 | 100 | 100 | 100 |
| | Concentration (wt-%) | | | | | | |
| Day 7, POAA, 20° C. | 10.4 | 9.17 | 8.87 | 8.36 | 10.8 | 8.53 | 6.86 |
| Day 14, POAA, 20° C. | 13.5 | 13.4 | 13.1 | 13.1 | 13.4 | 14.1 | 13.2 |
| Day 21, POAA, 20° C. | 13.5 | 13.5 | 14.3 | 14.0 | 13.8 | 14.3 | 14.2 |
| Day 28, POAA, 20° C. | 12.8 | 13.4 | 14.0 | 13.6 | 13.5 | 14.4 | 13.9 |
| Day 35, POAA, 20° C. | 12.4 | 12.8 | 13.5 | 13.6 | 13.1 | 14.1 | 13.8 |
| Day 7, $H_2O_2$, 20° C. | 5.92 | 6.34 | 6.33 | 6.53 | 5.37 | 6.76 | 7.26 |
| Day 14, $H_2O_2$, 20° C. | 4.03 | 4.35 | 4.33 | 4.41 | 3.80 | 4.24 | 4.19 |
| Day 21, $H_2O_2$, 20° C. | 3.67 | 3.68 | 3.82 | 3.75 | 3.57 | 3.71 | 3.61 |
| Day 28, $H_2O_2$, 20° C. | 3.44 | 3.41 | 3.45 | 3.49 | 3.37 | 3.58 | 3.56 |
| Day 35, $H_2O_2$, 20° C. | 3.20 | 3.32 | 3.33 | 3.22 | 3.31 | 3.39 | 3.27 |
| Day 7, POAA, 40° C. | 13.1 | 13.4 | 13.3 | 13.4 | 13.6 | * | * |
| Day 14, POAA, 40° C. | 11.2 | 7.45 | 12.2 | 12.3 | 12.0 | 12.8 | 13.0 |
| Day 21, POAA, 40° C. | 9.31 | 9.71 | 10.2 | 10.6 | 10.3 | 12.4 | 12.0 |
| Day 28, POAA, 40° C. | 8.00 | 8.36 | 9.11 | 9.42 | 9.27 | 11.9 | 10.9 |
| Day 35, POAA, 40° C. | 6.79 | 6.86 | 7.68 | 8.15 | 8.24 | 10.5 | 9.24 |
| Day 7, $H_2O_2$, 40° C. | 3.84 | 4.03 | 4.09 | 4.10 | 3.75 | * | * |
| Day 14, $H_2O_2$, 40° C. | 3.17 | 3.33 | 3.22 | 3.22 | 3.27 | 3.56 | 3.41 |
| Day 21, $H_2O_2$, 40° C. | 2.67 | 2.78 | 2.75 | 2.77 | 2.83 | 3.38 | 3.16 |
| Day 28, $H_2O_2$, 40° C. | 2.34 | 2.18 | 2.40 | 2.38 | 2.44 | 3.16 | 2.94 |
| Day 35, $H_2O_2$, 40° C. | 1.98 | 1.93 | 2.13 | 2.13 | 2.20 | * | 2.47 |

The results demonstrate that urea can maintain stability of both peroxide and peroxycarboxylic acid when utilized in formulations containing at least two peroxycarboxylic acids. As the concentration of urea increased, the stability of both peroxyacetic acid and hydrogen peroxide increased and/or maintained its concentration around 13 wt-% and 3 wt-% respectively. The results also demonstrated synergistic stabilization properties utilizing both urea and HEDP. Formulation U, which did not include urea, appeared to be the least effective in maintaining both hydrogen peroxide and peroxycarboxylic acid stability. Without being limited to a particular theory or mechanism, the addition of octanoic acid, resulting in a mixed peroxycarboxylic acid composition, presented additional stability challenges due to the higher concentration of total peroxycarboxylic acid present within the composition. However, as shown in the results, the compositions including urea provided superior stabilization of both hydrogen peroxide and peroxycarboxylic acid.

Example 4

Formulations containing both a peroxide and peroxycarboxylic acid were further evaluated, where the concentration of hydrogen peroxide was less than the concentration of acetic acid. Compositions were formulated utilizing urea and HEDP, with varying concentrations of sulfuric acid. The concentration of both hydrogen peroxide and peroxyacetic acid were evaluated over a period of 5 weeks at a temperature of both 20° C. and 40° C. At equilibrium, prior to decomposition, the concentration of peroxyacetic acid was about 15 wt-% and the concentration of hydrogen peroxide was about 11 wt-%.

The formulations are shown in Table 7 along with the stabilization results for each formulation. The results demonstrate the concentration of hydrogen peroxide and peroxyacetic acid present at day 4, day 14, day 21, day 28, and day 35.

TABLE 7

| Composition | Formulation (wt-%) | | | | | | |
| --- | --- | --- | --- | --- | --- | --- | --- |
|  | B1 | C1 | D1 | E1 | F1 | G1 | H1 |
| Water | 19.1 | 19.0 | 18.6 | 18.1 | 19.7 | 19.6 | 19.1 |
| $H_2O_2$, 50% | 35.6 | 35.6 | 35.6 | 35.6 | 35.6 | 35.6 | 35.6 |
| Acetic acid, 100% | 43.8 | 43.8 | 43.8 | 43.8 | 43.8 | 43.8 | 43.8 |
| HEDP, 60% | 1.50 | 1.50 | 1.50 | 1.50 | 0.80 | 0.80 | 0.80 |
| Sulfuric acid, 72% | 0.00 | 0.00 | 0.00 | 0.00 | 0.10 | 0.10 | 0.20 |
| Urea (bead) | 0.00 | 0.10 | 0.50 | 1.00 | 0.00 | 0.10 | 0.50 |
| Total | 100 | 100 | 100 | 100 | 100 | 100 | 100 |
|  | Concentration (wt-%) | | | | | | |
| Day 4, POAA, 20° C. | 11.5 | 11.4 | 10.4 | 9.92 | 10.2 | 10.1 | 9.67 |
| Day 14, POAA, 20° C. | 14.8 | 14.7 | 14.5 | 14.4 | 14.4 | 14.6 | 14.6 |
| Day 21, POAA, 20° C. | 15.0 | 15.0 | 15.1 | 14.9 | 14.8 | 14.9 | 15.0 |
| Day 28, POAA, 20° C. | 15.1 | 15.3 | 15.0 | 14.8 | 14.4 | 15.0 | 15.0 |
| Day 35, POAA, 20° C. | 15.1 | 15.2 | 15.3 | 15.0 | 14.9 | 14.9 | 15.1 |
| Day 4, $H_2O_2$, 20° C. | 12.7 | 12.8 | 13.2 | 13.4 | 13.3 | 13.3 | 13.6 |
| Day 14, $H_2O_2$, 20° C. | 11.2 | 11.3 | 11.2 | 11.4 | 11.4 | 11.4 | 11.6 |
| Day 21, $H_2O_2$, 20° C. | 11.0 | 11.0 | 11.1 | 11.2 | 11.2 | 11.1 | 11.2 |
| Day 28, $H_2O_2$, 20° C. | 11.0 | 11.0 | 11.0 | 11.1 | 11.1 | 11.1 | * |
| Day 35, $H_2O_2$, 20° C. | 11.0 | 11.1 | 11.1 | 11.1 | 11.1 | 11.1 | 11.2 |
| Day 14, POAA, 40° C. | 14.9 | 14.7 | 12.5 | 14.4 | 14.4 | 14.5 | 14.6 |
| Day 21, POAA, 40° C. | 15.2 | 14.8 | 14.9 | 14.7 | 14.9 | 14.9 | 14.8 |
| Day 28, POAA, 40° C. | 15.1 | 15.1 | 15.2 | 14.8 | 15.3 | 15.2 | 15.2 |
| Day 35, POAA, 40° C. | 15.1 | 15.3 | 15.3 | 15.0 | 15.2 | 15.4 | 15.3 |
| Day 14, $H_2O_2$, 40° C. | 11.1 | 11.2 | 11.2 | * | 11.3 | 11.4 | 11.1 |
| Day 21, $H_2O_2$, 40° C. | 11.1 | 11.1 | 11.1 | 11.0 | 11.3 | 11.2 | 11.1 |
| Day 28, $H_2O_2$, 40° C. | 10.8 | 10.8 | 10.9 | 10.6 | 11.0 | 11.0 | 11.0 |
| Day 35, $H_2O_2$, 40° C. | 10.7 | 10.9 | 10.7 | 10.5 | 10.9 | 11.0 | 10.9 |

The results demonstrate that the addition of urea to HEDP maintained both peroxide and peroxycarboxylic acid stability in formulations where the initial carboxylic acid concentration was greater than the hydrogen peroxide concentration. The results further demonstrate that urea and HEDP may be utilized together to stabilize compositions forming oxidizing compounds such as peroxide and peroxycarboxylic acid compositions.

Example 5

Additional formulations were evaluated to determine the ability of the urea stabilizing agent to reduce the concentration of additional stabilizing agents, while still maintaining effective stabilization. Peroxide-containing compositions were formulated with urea and HEDP, with varying combinations of oxidizing compounds. The concentration of both hydrogen peroxide and peroxyacetic acid were evaluated over a period of 5 weeks at a temperature of both 20° C. and 40° C.

The formulations are shown in Table 8 along with the stabilization results for each formulation. Formulations 1-1 and 1-2 demonstrate a direct comparison in a peroxide-containing composition comprising hydrogen peroxide, acetic acid, and octanoic acid, where 1-1 contains HEDP but does not contain urea, and 1-2 contains urea with a 50% reduction in HEDP. Formulations 2-1, 2-2, and 2-3 demonstrate a direct comparison in a peroxide-containing composition comprising hydrogen peroxide and acetic acid, where Formulation 2-1 contains HEDP but does not contain urea, 2-2 contains both HEDP and urea, and 2-3 contains urea with a 50% reduction in HEDP.

The results demonstrate the concentration of hydrogen peroxide and peroxycarboxylic acid present at day 4 or day 35. It is noted that the total moles of peroxygen was measured, however, due to the varying molecular weights of the mixed peroxycarboxylic acids present, the total concentration for the peroxycarboxylic acids are reported as a wt-% calculation of total peroxyacetic acid (i.e., shown as POAA).

TABLE 8

| Composition | Formulation (wt-%) | | | | |
|---|---|---|---|---|---|
| | 1-1 | 1-2 | 2-1 | 2-2 | 2-3 |
| DI Water | 9.00 | 8.80 | 19.1 | 18.6 | 19.2 |
| $H_2O_2$, 50% | 21.0 | 21.0 | 35.6 | 35.6 | 35.6 |
| Acetic acid, 100% | 59.0 | 59.0 | 43.8 | 43.8 | 43.8 |
| Octanoic acid | 10.0 | 10.0 | 0.00 | 0.00 | 0.00 |
| Urea (prilled) | 0.00 | 0.20 | 0.00 | 0.50 | 0.50 |
| HEDP, 60% | 1.00 | 0.50 | 1.50 | 1.50 | 0.75 |
| Sulfuric acid, 72% | 0.00 | 0.00 | 0.00 | 0.00 | 0.15 |
| Total | 100 | 100 | 100 | 100 | 100 |
| | Concentration (wt-%) | | | | |
| Day 4, POAA, 20° C. | * | * | 11.5 | 10.4 | 9.67 |
| Day 35, POAA, 20° C. | 13.1 | 13.8 | * | * | * |
| Day 35, $H_2O_2$, 20° C. | 3.31 | 3.27 | 11.0 | 11.1 | 11.2 |
| Day 35, POAA, 40° C. | 8.24 | 9.24 | 15.1 | 15.3 | 15.3 |
| Day 35, $H_2O_2$, 40° C. | 2.20 | 2.47 | 10.7 | 10.7 | 10.9 |

The results demonstrate that the inclusion of urea can reduce the required amount of HEDP in the composition without negatively affecting the stabilization of oxidizing compounds. The results from Table 8 demonstrate that the compositions containing urea with a 50% reduction of HEDP resulted in comparable or improved stability compared to compositions utilizing only HEDP. This demonstrates the efficacy of the present disclosure in utilizing urea to reduce the concentration of additional stabilizing agents required to stabilize oxidizing compounds within a peroxide-containing composition.

The disclosures being thus described, it will be obvious that the same may be varied in many ways. Such variations are not to be regarded as a departure from the spirit and scope of the disclosures and all such modifications are intended to be included within the scope of the following claims. The above specification provides a description of the manufacture and use of the disclosed compositions and methods. Since many embodiments can be made without departing from the spirit and scope of the disclosure, the disclosure resides in the claims.

What is claimed is:

1. A food safe stabilized equilibrium peroxide-containing composition comprising:
   from about 20 wt-% to about 70 wt % of hydrogen peroxide based on the total weight of the peroxide-containing composition;
   a $C_1$-$C_{22}$ peroxycarboxylic acid;
   a $C_1$-$C_{22}$ carboxylic acid;
   a stabilizing agent comprising urea;
   an additional stabilizing agent and/or an acid additive comprising an organic acid, an inorganic acid, or a combination thereof; and
   water;
   wherein the urea stabilizes the peroxide-containing composition without an additional stabilizing agent or reduces the concentration of the additional stabilizing agent to less than 3 wt-%.

2. The composition of claim 1, wherein the peroxide-containing composition comprises the urea in an amount of from about 0.01 wt-% to about 5 wt-%, the $C_1$-$C_{22}$ peroxycarboxylic acid in an amount of from about 3 wt-% to about 25 wt-%, the $C_1$-$C_{22}$ carboxylic acid in an amount of from about 1 wt-% to 80 wt-%, and the water in an amount from about 1 wt-% to 50 wt-%.

3. The composition of claim 2, wherein the $C_1$-$C_{22}$ peroxycarboxylic acid is a $C_2$-$C_{20}$ peroxycarboxylic acid.

4. The composition of claim 2, wherein the $C_1$-$C_{22}$ carboxylic acid is a $C_2$-$C_{20}$ carboxylic acid.

5. The composition of claim 1, wherein the peroxycarboxylic acid is peroxyacetic acid, peroxyoctanoic acid and/or peroxysulfonated oleic acid.

6. The composition of claim 1, wherein the carboxylic acid is acetic acid, octanoic acid and/or sulfonated oleic acid.

7. The composition of claim 1, wherein the peroxide-containing composition comprises the additional stabilizing agent which comprises 1-hydroxyethylidene-1,1-diphosphonic acid (HEDP).

8. The composition of claim 7, wherein the HEDP is present in an amount of from about 0.01 wt-% to about 3 wt-% of the composition.

9. The composition of claim 7, wherein the urea stabilizing agent reduces the amount of HEDP included in the composition to less than 34 ppm in a use solution.

10. The composition of claim 1, wherein the peroxide-containing composition is free of any material that is not considered to be a GRAS or food additive ingredient.

11. The composition of claim 1, further comprising at least one additional functional ingredient comprising a surfactant, a hydrotrope, a defoaming agent, an additional solvent, an additional acid additive, antimicrobial agents, bleaching agents, or a combination thereof.

12. The composition of claim 1, wherein at least 80% of the oxidizing compound concentrations are retained when stored at room temperature for one year.

13. A method of stabilizing a peroxide-containing composition comprising:
   combining an oxidizing compound which is hydrogen peroxide, a C1-C22 peroxycarboxylic acid, C1-C22 carboxylic acid, a stabilizing agent comprising urea, an additional stabilizing agent and/or an acid additive comprising an organic acid, an inorganic acid, or a combination thereof; and water, wherein hydrogen peroxide is present in an amount from about 20 wt. % to about 70 wt. % based on the total weight of the peroxide-containing composition;
   wherein at least 80% of the oxidizing compound concentration is retained after storage of up to one year at room temperature, and wherein the urea stabilizes the peroxide containing composition without an additional stabilizing agent or reduces the concentration of the additional stabilizing agent to less than 3 wt. %.

14. The method of claim 13, wherein at least 85% of the oxidizing compound concentration is retained after storage of about one year at room temperature.

15. The method of claim 13, wherein the oxidizing compound is stabilized without the use of a pyridine carboxylic acid.

16. The method of claim 13, wherein the $C_1$-$C_{22}$ peroxycarboxylic acid is a $C_2$-$C_{20}$ peroxycarboxylic acid comprising peroxyacetic acid, peroxyoctanoic acid, peroxysulfonated oleic acid, or a combination thereof.

17. The method of claim 13, wherein the $C_1$-$C_{22}$ carboxylic acid is a $C_2$-$C_{20}$ carboxylic acid comprising acetic acid, octanoic acid, sulfonated oleic acid, or a combination thereof.

18. The method of claim 13, wherein the peroxide-containing composition comprises the additional stabilizing agent which comprises HEDP.

19. The method of claim 18, wherein the urea stabilizing agent reduces the concentration of HEDP by at least 40% compared to a composition free of urea as the stabilizing agent.

* * * * *